(12) United States Patent
Buck et al.

(10) Patent No.: US 10,568,896 B2
(45) Date of Patent: Feb. 25, 2020

(54) METHODS FOR PREVENTING OR MITIGATING ACUTE ALLERGIC RESPONSES USING HUMAN MILK OLIGOSACCHARIDES

(71) Applicant: Abbott Laboratories, Abbott Park, IL (US)

(72) Inventors: Rachael Buck, Gahanna, OH (US); Steven Davis, Galena, OH (US); Paul Forsythe, Hamilton (CA)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 15/037,743

(22) PCT Filed: Nov. 18, 2014

(86) PCT No.: PCT/US2014/066162
§ 371 (c)(1),
(2) Date: May 19, 2016

(87) PCT Pub. No.: WO2015/077233
PCT Pub. Date: May 28, 2015

(65) Prior Publication Data
US 2016/0296544 A1  Oct. 13, 2016

Related U.S. Application Data

(60) Provisional application No. 61/905,952, filed on Nov. 19, 2013.

(51) Int. Cl.
| *A61K 31/702* | (2006.01) |
| *A23L 33/125* | (2016.01) |
| *A23L 5/00* | (2016.01) |
| *A61K 45/06* | (2006.01) |
| *A23L 29/30* | (2016.01) |
| *A61K 31/7016* | (2006.01) |
| *A61K 31/4545* | (2006.01) |
| *A61K 31/495* | (2006.01) |
| *A61K 31/445* | (2006.01) |
| *A23L 33/10* | (2016.01) |
| *A23L 33/00* | (2016.01) |
| *A23L 33/21* | (2016.01) |
| *A23L 33/115* | (2016.01) |
| *A23L 29/00* | (2016.01) |
| *A23L 21/00* | (2016.01) |

(52) U.S. Cl.
CPC ............ *A61K 31/702* (2013.01); *A23L 5/00* (2016.08); *A23L 29/04* (2016.08); *A23L 29/045* (2016.08); *A23L 29/30* (2016.08); *A23L 33/10* (2016.08); *A23L 33/115* (2016.08); *A23L 33/125* (2016.08); *A23L 33/21* (2016.08); *A23L 33/40* (2016.08); *A61K 31/445* (2013.01); *A61K 31/4545* (2013.01); *A61K 31/495* (2013.01); *A61K 31/7016* (2013.01); *A61K 45/06* (2013.01); *A23L 21/00* (2016.08); *A23V 2002/00* (2013.01); *A23V 2200/00* (2013.01); *A23V 2250/00* (2013.01)

(58) Field of Classification Search
None
See application file for complete search history.

(56) References Cited

U.S. PATENT DOCUMENTS

| 5,527,785 | A | 6/1996 | Bevilacqua et al. |
| 5,891,698 | A | 4/1999 | Prieto et al. |
| 6,291,435 | B1 | 9/2001 | Yanmaele et al. |
| 6,306,908 | B1 | 10/2001 | Carlson et al. |
| 6,365,218 | B1 | 4/2002 | Borschel et al. |
| 6,384,038 | B1 * | 5/2002 | Rubin ............... A61K 31/495 514/255.04 |
| 6,630,452 | B2 | 10/2003 | Wilson |
| 7,893,041 | B2 | 2/2011 | Morrow et al. |
| 8,314,061 | B2 | 11/2012 | Morrow et al. |
| 8,394,370 | B2 | 3/2013 | Garcia-Rodenas et al. |
| 2003/0118703 | A1 | 6/2003 | Nguyen et al. |
| 2004/0072794 | A1 | 4/2004 | Kaup et al. |
| 2007/0269833 | A1 | 11/2007 | Minamisawa et al. |
| 2009/0098240 | A1 | 4/2009 | Mills et al. |
| 2010/0047393 | A1 | 2/2010 | Glas et al. |
| 2010/0260720 | A1 | 10/2010 | Sprenger |
| 2011/0177044 | A1 | 7/2011 | Thomas et al. |
| 2011/0195025 | A1 | 8/2011 | Kett et al. |
| 2011/0207659 | A1 | 8/2011 | Morrow et al. |
| 2011/0223201 | A1 | 9/2011 | Lipford et al. |

(Continued)

FOREIGN PATENT DOCUMENTS

| EP | 1550448 | 7/2005 |
| EP | 2217253 | 6/2011 |

(Continued)

OTHER PUBLICATIONS

"35 Breast Milk Home Remedies", Apr. 2012, retrieved from: http://www.simplyrealmoms.com/posts/33-uses-for-breast-milk/ on Dec. 18, 2017 (Year: 2012).*
Bischoff, S. C. (2007). Role of mast cells in allergic and non-allergic immune responses: comparison of human and murine data. Nature Reviews Immunology, 7(2), 93-104. (Year: 2007).*

(Continued)

*Primary Examiner* — Dale R Miller
(74) *Attorney, Agent, or Firm* — Calfee, Halter & Griswold LLP (57) ABSTRACT

A method for preventing or mitigating an acute allergic response in a subject is disclosed. The method includes a step of administering a nutritional composition to the subject. The nutritional composition includes at least one of an acidic or a neutral HMO, but does not include an N-acetyl-lactosamine.

18 Claims, 6 Drawing Sheets

(56) References Cited

U.S. PATENT DOCUMENTS

| | | |
|---|---|---|
| 2012/0171165 A1 | 7/2012 | Buck et al. |
| 2012/0172307 A1 | 7/2012 | Davis et al. |
| 2012/0172319 A1 | 7/2012 | Chow et al. |
| 2012/0172327 A1 | 7/2012 | Buck et al. |
| 2012/0177691 A1 | 7/2012 | Stahl et al. |
| 2012/0178674 A1 | 7/2012 | Stahl et al. |
| 2012/0184503 A1 | 7/2012 | Buck et al. |
| 2012/0202753 A1 | 8/2012 | Morrow et al. |
| 2012/0294840 A1 | 11/2012 | Newburg et al. |

FOREIGN PATENT DOCUMENTS

| | | |
|---|---|---|
| EP | 2455387 | 5/2012 |
| WO | 2012069415 | 5/2012 |
| WO | 2012069416 | 5/2012 |
| WO | 2012076321 | 6/2012 |
| WO | 2012076322 | 6/2012 |
| WO | 2012156273 | 11/2012 |
| WO | 2013025104 | 2/2013 |

OTHER PUBLICATIONS

"Prevention" in Glossary of medical education terms: Parts 1-7. Wojtczak, A., Ed. Medical Teacher. vol. 24, Nos. 2-6 and vol. 25, No. 1&2. 2002. (Year: 2002).*

Castillo-Courtade, L., Han, S., Lee, S., Mian, F. M., Buck, R., & Forsythe, P. (2015). Attenuation of food allergy symptoms following treatment with human milk oligosaccharides in a mouse model. Allergy, 70(9), 1091-1102. (Year: 2015).*

Bischoff, S., & Crowe, S. E. (2005). Gastrointestinal food allergy: new insights into pathophysiology and clinical perspectives. Gastroenterology, 128(4), 1089-1113. (Year: 2005).*

International Search Report and Written Opinion from PCT/US2014/066162 dated Feb. 2, 2015.

International Preliminary Report on Patentability from PCT/US2014/066162 dated May 24, 2016.

Bax et al., "Campylobacter jejuni Lipooligosaccharides Modulate Dendritic Cell-Mediated T Cell Polarization in a Sialic Acid Linkage-Dependent Manner" Infection and Immunity, Jul. 2011, vol. 79, No. 7, pp. 2681-2689.

Brown et al., "Mast cells as important modifies of autoimmune disease: with so much evidence, why is there still controversy?" Frontiers in Immunology, Jun. 2012, vol. 3, Article 147, pp. 1-14.

Eiwegger et al., "Prebiotic oligosaccharides: in vitro evidence for gastrointestinal epithelial transfer and immunomodulatory properties," Pediatric Allergy and Immunology, Dec. 2010, vol. 21, No. 8, pp. 1179-1188.

Jeurink et al, "Difficulties in Describing Allergic Disease Modulation by Pre-, Pro- and Synbiotics," Current Pharmaceutical Design, 2012, vol. 18, No. 16, pp. 2369-2374.

* cited by examiner

METHODS FOR PREVENTING OR MITIGATING ACUTE ALLERGIC RESPONSES USING HUMAN MILK OLIGOSACCHARIDES

CROSS-REFERENCE TO RELATED APPLICATIONS

This application is the U.S. national phase entry of PCT/US2014/066162, with an international filing date of Nov. 18, 2014, which claims priority to and any benefit of U.S. Provisional Application No. 61/905,952, filed Nov. 19, 2013, the entire contents of which are incorporated by reference in their entirety.

FIELD OF THE DISCLOSURE

The disclosure relates to methods for preventing or mitigating acute allergic responses in a subject. Particularly, the disclosure relates to the use of nutritional compositions comprising human milk oligosaccharides to prevent or mitigate an acute allergic response in the subject.

BACKGROUND

The maintenance of a balanced immune system is important to human health. On the one hand, reduced immunity can leave an individual vulnerable to attack from foreign microorganisms. On the other, individuals with hyper-active immune systems can suffer from mild to severe allergies. Common allergic symptoms include sneezing, asthma, diarrhea, skin itching, hives, and angioedema. In rare cases, allergies can result in severe or deadly symptoms such as anaphylactic shock. While allergies can be a mild irritant, they can also have a significant impact on an individual's daily activities and quality of life. Although allergies typically develop during childhood, allergies may develop at any time during an individual's lifespan.

A limited number of treatments exist to address the problem of allergies. In some patient populations, certain allergies can be treated with pharmaceuticals, including antihistamines and eicosanoid inhibitors. Despite available treatment options, the prevalence of allergies in the global population is increasing, such that allergies are now considered an epidemic by The World Health Organization.

There are likely several reasons for the increase in allergies among global populations. First, available treatment options are often inappropriate for all populations. For example, due to potential side effects, pharmaceuticals may be inappropriate for children and infants, a population in which allergies are highly prevalent and ever-increasing. Second, available treatment options do not address all types of allergies. For example, food allergies, in particular, have no effective drug therapy. As a result, avoidance of the triggering foods or antigens is often the only course of action for affected individuals. Third, available treatment options do not fully address the underlying causes of allergies. For example, the nervous system plays an important role in regulating immune responses associated with allergic inflammation as well as gastrointestinal symptoms associated with a food allergy. While antihistamines address the immune system's role in an allergic response, they do not address the actions of the nervous system. Fourth, some treatment options may decrease natural defenses that help prevent allergic responses. For example, increasing antibiotic use in industrialized countries may disrupt normal microbiota-mediated mechanisms of immunological tolerance in the mucosa. This disruption of the natural microbiome can, in turn, lead to an increased susceptibility to immunological disorders including allergy.

It would be desirable to provide additional treatment options to reduce the risk of allergy development, help in the management of allergic disease, or both. Such treatments may reduce the severity of symptoms, increase the antigen exposure levels required to trigger allergic responses, or both. To be useful across patient populations, it would be beneficial to provide a benign approach to allergy treatment. To treat various types of allergies, it would be useful for the treatment to be available as multiple formulations such as nutritionals, dietary supplements, or topical products. Where pharmaceuticals are useful, it would be helpful to provide new treatments that complement existing pharmaceutical approaches to allergy control. Where pharmaceuticals are inappropriate or ineffective, it is desirable to offer alternative approaches to allergic disease management. To support natural defenses to allergies, it would be helpful for the treatment options to promote the body's natural microbiome, or to help reestablish it, or both.

SUMMARY

Disclosed herein are methods for preventing or mitigating an acute allergic response in a subject. An acute allergic response is prevented or mitigated by administering human milk oligosaccharides (HMOs) to the subject.

A method for preventing or mitigating an acute allergic response in a subject is disclosed. The method includes a step of administering a nutritional composition to the subject. The nutritional composition includes at least one of an acidic or a neutral HMO, but does not include an N-acetyl-lactosamine.

The present invention provides a method for preventing or mitigating an acute allergic response in a subject, the method comprising administering a nutritional composition to the subject, wherein the nutritional composition comprises at least one human milk oligosaccharide (HMO) selected from the group consisting of acidic HMOs and neutral HMOs, and wherein the nutritional composition does not contain an N-acetyl-lactosamine.

The present invention also provides a nutritional composition for use in the prevention, treatment and/or mitigation of an acute allergic response in a subject, wherein the nutritional composition comprises at least one human milk oligosaccharide (HMO) selected from the group consisting of acidic HMOs and neutral HMOs, and wherein the nutritional composition does not contain an N-acetyl-lactosamine.

In the specification, references to the method also apply to the composition where applicable, and vice versa.

Further areas of applicability of the present disclosure will become apparent from the detailed description, drawings, and claims provided hereinafter. It should be understood that the detailed description, including disclosed embodiments and drawings, are merely exemplary in nature, are only intended for purposes of illustration, and are not intended to limit the scope of the invention, its application, or use.

DETAILED DESCRIPTION

The term "administering," unless otherwise indicated herein, should be understood to include: a) providing the nutritional composition to a subject, b) the act of consuming the nutritional product, and combinations thereof.

The term "nutritional composition" as used herein, unless otherwise specified, refers to nutritional products in various forms including, but not limited to, liquids, solids, powders, semi-solids, semi-liquids, nutritional supplements, and any other nutritional food product known in the art. A nutritional composition in powder form may be reconstituted upon addition of water or another liquid to form a liquid nutritional composition prior to administration to (e.g., providing to or consumption by) a subject. As discussed below, in certain embodiments disclosed herein, the nutritional compositions comprise at least one of a source of protein, a source of carbohydrate, and a source of fat. The nutritional compositions disclosed herein are generally suitable for oral consumption by a human.

The term "subject," unless otherwise indicated herein, refers to a mammal, including, but not limited to, a human, a domesticated farm animal (e.g., cow, horse, pig), or a pet (e.g., dog, cat). In certain embodiments disclosed herein, the subject is a human.

The term "human milk oligosaccharide" or "HMO", as used herein, unless otherwise specified, refers generally to a number of complex carbohydrates found in human breast milk that can be in acidic or neutral form, and to precursors thereof. Exemplary non-limiting human milk oligosaccharides include 3'-sialyllactose, 6'-sialyllactose, 3'-fucosyllactose, and 2'-fucosyllactose. Exemplary human milk oligosaccharide precursors includes sialic acid, fucose, and combinations thereof. As a natural constituent of human breast milk, HMOs are largely believed to be benign in character. "HMO" includes "acidic HMOs," e.g., sialylated oligosaccharides, and "neutral HMOs," e.g., fucosylated oligosaccharides.

"Acute allergic response" means an allergic condition of the immediate type (in human or animals).

A "mast cell mediated immediate allergic response" is an acute allergic response resulting from the actions of the mast cells. The response may result from actions of mast cells in one or more tissue types. Such responses occur shortly (i.e., within seconds to minutes) after exposure to an antigen and include those caused by immunoglobulin E (IgE).

Disclosed herein are methods for preventing or mitigating an acute allergic response in a subject. The acute allergic response is prevented or mitigated in the subject by administering a nutritional composition to the subject. In particular, the nutritional composition administered to the subject includes at least one of an acidic or neutral HMO, but the nutritional composition does not include an N-acetyl-lactosamine.

Methods disclosed herein can be used to mitigate or prevent any number of acute allergic responses. In particular embodiments, the acute allergic responses can include one or more mast cell mediated immediate allergic response. Such responses include those that are IgE mediated. Exemplary, but non-limiting allergic responses that can be mitigated or prevented include eosinophilic gastroenteritis, eosinophilic esophagitis, and enterocolitis. The methods disclosed herein can be used to maintain proper immune system function, increase tolerance levels to potential allergens, reduce allergy-associated inflammation, or combinations thereof, and, thereby prevent or mitigate allergic symptoms in a subject.

The disclosed methods can be carried out using any of a number of HMOs known in the art. The methods may involve administering one or more HMOs alone or in combination with other compounds used in nutritional compositions. HMOs include the oligosaccharides found in human breast milk. Suitable HMOs for use with the disclosed methods include any acidic or neutral HMO, including HMO precursors. Specific non-limiting examples of HMOs include sialic acid (i.e., free sialic acid, lipid-bound sialic acid, protein-bound sialic acid); D-glucose (Glc); D-galactose (Gal); L-fucose (Fuc); fucosyl oligosaccharides (i.e., Lacto-N-fucopentaose I; Lacto-N-fucopentaose II; 2'-Fucosyllactose; 3'-Fucosyllactose; Lacto-N-fucopentaose III; Lacto-N-difucohexaose I; and Lactodifucotetraose); sialyl oligosaccharides (i.e., 3'-Sialyl-3-fucosyllactose; Disialomonofucosyllacto-N-neohexaose; Monofucosyl-monosialyllacto-N-octaose (sialyl Lea); Sialyllacto-N-fucohexaose II; Disialyllacto-N-fucopentaose II; Monofucosyl-disialyllacto-N-tetraose); and sialyl fucosyl oligosaccharides (i.e., 2'-Sialyllactose; 2-Sialyllactosamine; 3'-Sialyllactose; 3'-Sialyllactosamine; 6'-Sialyllactose; 6'-Sialyllactosamine; Sialyllacto-N-neotetraose c; Monosialyllacto-N-hexaose; Disialyllacto-N-hexaose I; Monosialyl-lacto-N-neohexaose I; Monosialyllacto-N-neohexaose II; Disialyllacto-N-neohexaose; Disialyllacto-N-tetraose; Disialyllacto-N-hexaose II; Sialyllacto-N-tetraose a; Disialyllacto-N-hexaose I; and Sialyllacto-N-tetraose b). These HMOs are described more fully in U.S. Patent Application Publication No. 2009/0098240, which is hereby incorporated by reference herein in its entirety. Other suitable examples of HMOs that may be included in the compositions of the present disclosure include lacto-N-fucopentaose V, sialyl-lacto-N-tetraose a, sialyl-lacto-N-tetraose b, sialyl-lacto-N-tetraose c, sialyl-fucosyl-lacto-N-tetraose I, sialyl-fucosyl-lacto-N-tetraose II, and disialyl-lacto-N-tetraose, and combinations thereof. Particularly suitable nutritional compositions include at least one of the following HMOs or HMO precursors: sialic acid (SA); 6'-Sialyllactose; 2'-Fucosyllactose; and in particular, combinations of 6'-Sialyllactose and 2'-Fucosyllactose.

The HMO or HMOs used in the nutritional compositions may be isolated or enriched from milk(s) secreted by mammals including, but not limited to: human, bovine, ovine, porcine, or caprine species. The HMOs may also be produced via microbial fermentation, enzymatic processes, chemical synthesis, or combinations thereof.

In some embodiments, the HMOs are present in the nutritional compositions in total amounts of HMO in the nutritional composition (mg of HMO per mL of nutritional composition) of at least about 0.001 mg/mL, including at least about 0.01 mg/mL, including from about 0.001 mg/mL to about 20 mg/mL, including from about 0.01 mg/mL to about 20 mg/mL, including from about 0.001 mg/mL to about 10 mg/mL, including from about 0.01 mg/mL to about 10 mg/mL, including from about 0.001 mg/mL to about 5 mg/mL, including from about 0.01 mg/mL to about 5 mg/mL, including from about 0.001 mg/mL to about 1 mg/mL, including from about 0.001 mg/mL to about 0.23 mg/mL, including from about 0.01 mg/mL to about 0.23 mg/mL of total HMO in the nutritional composition. Typically, the amount of HMO in the nutritional composition will depend on the specific HMO or HMOs present and the amounts of other components in the nutritional composition.

Applicants have unexpectedly discovered that particular HMOs can be used to mitigate or prevent particular mast cell mediated immediate allergic responses. As a result, in some embodiments, the disclosure provides methods targeted to mitigating or preventing particular allergic response(s) in a subject using particularized combinations of HMOs.

In particular embodiments, a nutritional composition including the acidic HMO 6'-sialyllactose (6'-SL) and the neutral HMO 2'-fucosyllactose (2'-FL) each, separately, or in combination, is used to mitigate or prevent the allergies in a subject suffering from one or more mast cell mediated immediate allergic response involving skin mast cells, gastrointestinal mast cells, respiratory mast cells, or combinations thereof.

In some embodiments where 6'-SL is present alone or in combination with other HMOs, it is present in an amount from about 0.001 mg/mL to about 20 mg/mL, including from about 0.01 mg/mL to about 20 mg/mL, including from about 0.001 mg/mL to less than about 0.25 mg/mL, including from about 0.01 mg/mL to less than or equal to about 0.25 mg/mL, including from greater than or equal to about 0.25 mg/mL to about 20 mg/mL, and including from about 0.1 mg/mL to about 0.5 mg/mL.

In some embodiments where 2'-FL is present alone or in combination with other HMOs, it is present in an amount of from about 0.001 mg/mL to about 20 mg/mL, including from about 0.01 mg/mL to about 20 mg/mL, including from about 0.001 mg/mL to about 2.5 mg/mL, and including from about 0.01 mg/mL to about 2.5 mg/mL. In another embodiment, the nutritional composition includes 2'-FL, alone or in combination with other HMOs, in an amount of from about 0.001 mg/mL to about 20 mg/mL, including from about 0.01 mg/mL to about 20 mg/mL and including greater than 2.5 mg/mL to about 20 mg/mL.

In a specific embodiment, a subject suffering from only a single mast cell mediated immediate allergic response is administered a nutritional composition including either 6'-SL or 2'-FL, but not both. In a particularly specific embodiment, a subject suffering from a single mast cell mediated immediate allergic response is administered a nutritional composition including 2'-FL and not 6'-SL. In an even more specific embodiment, a nutritional composition including 2'-FL and not 6'-SL is administered to a subject when the subject suffers from a mast cell mediated immediate allergic response involving only gastrointestinal mast cells. In another embodiment, a nutritional composition including one of either 6'-SL or 2'-FL, but not both, is administered to a subject suffering from a mast cell mediated immediate allergic response involving only skin mast cells.

In another embodiment, a subject suffering from more than one mast cell mediated immediate allergic response is administered a nutritional composition including either one of 6'-SL or 2'-FL or both, based on the combination of mast cell mediated immediate allergic responses involved. In a more specific embodiment, a subject suffering from more than one mast cell mediated immediate allergic response is administered a nutritional composition including both 6'-SL and 2'-FL.

In other embodiments, the HMOs may be administered as part of a nutritional composition that includes an energy source. The energy source can include one or more of a protein source, a carbohydrate source, or a fat source.

In those embodiments where the nutritional composition includes a protein source, the protein source can include one or more of whey protein concentrates, whey protein isolates, whey protein hydrolysates, acid caseins, sodium caseinates, calcium caseinates, potassium caseinates, casein hydrolysates, milk protein concentrates, milk protein isolates, milk protein hydrolysates, nonfat dry milk, condensed skim milk, soy protein concentrates, soy protein isolates, soy protein hydrolysates, pea protein concentrates, pea protein isolates, pea protein hydrolysates, collagen proteins, potato proteins, rice proteins, fungal proteins, proteins expressed by microorganisms, and combinations thereof.

In those embodiments where the nutritional composition includes a carbohydrate source, the carbohydrate source can include one or more of maltodextrin; hydrolyzed or modified starch or cornstarch; glucose polymers; corn syrup; corn syrup solids; rice-derived carbohydrates; high fructose corn syrup; honey; sugar alcohols, such as maltitol, erythritol, sorbitol, glycerine; sucrose; glucose; fructose; lactose; isomaltulose, sucromalt, pullulan, potato starch, and other slowly-digested carbohydrates; oligosaccharides such as fructo-oligosaccharides; dietary fibers including, but not limited to, oat fiber, soy fiber, gum arabic, sodium carboxymethylcellulose, methylcellulose, guar gum, gellan gum, locust bean gum, konjac flour, hydroxypropyl methylcellulose, tragacanth gum, karaya gum, gum acacia, chitosan, arabinoglactins, glucomannan, xanthan gum, alginate, pectin, low and high methoxy pectin, cereal beta-glucans, carrageenan and psyllium, soluble dietary fibers such as digestion resistant maltodextrins, resistant modified food starches, other resistant starches; soluble and insoluble fibers derived from fruits or vegetables; and combinations thereof.

In some embodiments, it is desirable that the nutritional composition be low in lactose. Nutritional compositions that are low in lactose preferably have less than about 55% lactose relative to total carbohydrate, more preferably, less than about 45% lactose, more preferably less than about 35% lactose, more preferably less than about 25% lactose, and even more preferably less than about 15% lactose. In some embodiments where the administered nutritional composition is low in lactose, other carbohydrates are used in the nutritional composition. In particular embodiments, nutritional compositions low in lactose include one or more of maltodextrin, corn syrup solids, and sucrose.

In those embodiments where the nutritional composition includes a fat source, the fat source can include one or more of coconut oil, fractionated coconut oil, soy oil, corn oil, olive oil, safflower oil, high oleic safflower oil, medium chain triglyceride oil, high gamma linolenic safflower oil, sunflower oil, high oleic sunflower oil, palm oil, palm kernel oil, palm olein, canola oil, marine oils, algal oils, cottonseed oils, interesterified oils, transesterified oils, and combinations thereof.

The methods disclosed herein may involve administering the nutritional composition in any manner that allows for mitigation or prevention of an acute allergic response in a subject, where the manner of administration will depend on the type(s) of mast cell mediated immediate allergic response to be mitigated or prevented.

In some embodiments, the methods involve orally administering the nutritional composition to a subject. Oral administration, as defined herein, includes any form of administration in which the nutritional composition passes through the esophagus of the subject. For example, oral administration typically refers to oral consumption, but may also include nasogastric intubation, in which a tube is run from the nose to the stomach of the subject to administer the composition. In accordance with the embodiments described herein, suitable forms of the composition for oral administration to the subject include caplets, tablets, pills, capsules, chewable tablets, quick dissolve tablets, effervescent tablets, solutions, suspensions, emulsions, multi-layer tablets, bi-layer tablets, soft gelatin capsules, hard gelatin capsules, lozenges, chewable lozenges, beads, granules, particles, microparticles, dispersible granules, sachets, and combinations thereof. Oral administration is particularly suitable for subjects suffering from gastrointestinal mast cell mediated immediate allergic responses.

In other embodiments, the methods involve topically administering the nutritional composition to a subject. Topical administration involves applying the nutritional composition to an impacted area. Common forms of topical administration include, but are not limited to, drops, sprays, creams, ointments, lotions, pastes, jellies, aerosols, and bath oils. Topical administration is particularly suitable in subjects where tissue impacted by an allergic response is directly accessible, accessible through a body cavity, or proximate to either, e.g., in subjects suffering from respiratory or skin mast cell mediated immediate allergic responses.

In addition to administering the disclosed nutritional compositions, in some embodiments, the methods disclosed herein include the administration of other compounds to a subject. These compounds can either be part of the nutritional composition, or provided as separate compounds. In those embodiments where the nutritional composition and the other compounds are separate compounds, they may be administered together, i.e., in a single administration step, or in separate steps. Where the other compounds and the nutritional compositions are administered separately, either the nutritional compositions or the other compounds may be administered first.

Other compounds that can be administered to subjects to whom the nutritional compounds are administered include, e.g., vitamins, minerals, preservatives, antioxidants, buffers, pharmaceutical actives, additional nutrients, colorants, flavors, emulsifiers, prebiotics, and anti-foam agents.

In those embodiments where vitamins are administered in addition to, along with, or as part of the nutritional compositions, the administered vitamins can include curcumin, lutein, fish oil, vitamin A, vitamin D (cholecalciferol, 25-hydroxycholecalciferol, 1,25-dihydroxycholecalciferol, 24,25-dihydroxycholecalciferol, ergocalciferol), vitamin E, vitamin K, thiamine, riboflavin, pyridoxine, vitamin B12, carotenoids, niacin, folic acid, pantothenic acid, biotin, vitamin C, choline, inositol, salts, derivatives thereof, and combinations thereof.

In those embodiments where minerals are administered in addition to, along with, or as part of the nutritional compositions, the administered vitamins can include phosphorus, magnesium, iron, manganese, copper, sodium, potassium, molybdenum, chromium, selenium, chloride, zinc, and combinations thereof.

In particular embodiments, where pharmaceutical actives are administered in addition to, along with, or as part of the disclosed nutritional compositions, the pharmaceutical actives may include one or more antihistamine compounds. Many such compounds are known in the art, e.g., acrivastine, alimemazine, antazoline, astemizole, azatadine, azelastine, bamipine, bromazine, brompheniramine, bromodiphenhydramine, buclizine, carbinoxamine, cetirizine, chlorcyclizine, chloropyramine, chlorpheniramine, chlorphenoxamine, cinnarizine, clemastine, cyclizine, cyproheptadine, deptropine, desloratadine, dexbrompheniramine, dexchlorpheniramine, dimetindene, diphenhydramine, diphenylpyraline, doxylamine, dimenhydrinate, ebastine, histapyrrodine, hydroxyethylpromethazine, hydroxyzine, isothipendyl, ketotifen, loratadine, levocetirizine, mebhydrolin, meclizine, mepyramine, mequitazine, methapyrilene, methdilazine, mizolastine, niaprazine, oxomemazine, oxatomide, phenindamine, pheniramine, pimethixene, promethazine, pyribenzamine, pyrilamine, pyrrobutamine, rupatadine, talastine, terfenadine, thonzylamine, trimeprazine and tripelennamine. In preferred embodiments, the antihistamine compounds are one or more widely available antihistamine compounds including loratadine, fexofenadine, and cetirizine.

In those embodiments where an antihistamine compound is administered to a subject, the HMOs administered as part of the nutritional compositions may complement the ability of the antihistamine compounds to prevent or mitigate an allergic response in the subject. Without being bound by theory, the HMOs may complement the activity of the antihistamine compounds by targeting different cellular systems (e.g., regulation of the nervous and immune systems by HMOs versus regulation of only the immune system by antihistamines), different aspects of a given cellular system (e.g., regulation of mast cell degranulation or promotion of immune system stabilizing microbiota by HMOs versus suppression of histamine release by antihistamines, all within the immune system), or both.

In other embodiments, one or more eicosanoid inhibitors may be administered in addition to, along with, or as part of the disclosed nutritional compositions. Eicosanoid inhibitors can act on any number of eicosanoid compounds. In particular embodiments, the eicosanoid inhibitors administered inhibit one or more of thromboxanes, prostaglandins, and leukotrienes. The eicosanoid inhibitors can be any of the many eicosanoid inhibitors known in the art. In particular embodiments, the eicosanoid inhibitors include docosahexaenoic acid and eicosapentaenoic acid.

In other embodiments, it is desirable to further enhance the microbiota-stimulating activity of HMOs. In these embodiments, prebiotics may be administered in addition to, along with, or as part of the disclosed nutritional compositions. Commonly known prebiotics include fructo-oligosaccharides and galacto-oligosaccharides. Prebiotics help promote the body's microbiota by providing non-digestible food products for bacteria in the colon. To prevent administered prebiotics from eliciting an immune response, in some embodiments, it is preferred that prebiotics used be in a hypoallergenic form, i.e., in a form which is unlikely to cause allergies.

The nutritional compositions administered in the methods disclosed herein can be made by methods known in the art. Such methods are disclosed in various patent application publications and patents including U.S. Patent Publication 2012/0172307 A1, U.S. Pat. Nos. 6,365,218, 6,306,908, and U.S. Patent Publication 2003/0118703 A1, each of which is incorporated herein by reference for the disclosure of such methods.

In one suitable manufacturing process, for example, at least three separate slurries are prepared, including a protein-in-fat (PIF) slurry, a carbohydrate-mineral (CHO-MIN) slurry, and a protein-in-water (PIW) slurry. The PIF slurry is formed by heating and mixing the oil (e.g., canola oil, corn oil, etc.) and then adding an emulsifier (e.g., lecithin), fat soluble vitamins, and a portion of the total protein (e.g., milk protein concentrate, etc.) with continued heat and agitation. The CHO-MIN slurry is formed by adding with heated agitation to water minerals (e.g., potassium citrate, dipotassium phosphate, sodium citrate, etc.), trace and ultra trace minerals (TM/UTM premix), thickening or suspending agents (e.g. avicel, gellan, carrageenan). The resulting CHO-MIN slurry is held for 10 minutes with continued heat and agitation before adding additional minerals (e.g., potassium chloride, magnesium carbonate, potassium iodide, etc.), and/or carbohydrates (e.g., HMOs, fructooligosaccharide, sucrose, corn syrup, etc.). The PIW slurry is then formed by mixing with heat and agitation the remaining protein, if any. The resulting slurries are then blended together with heated agitation and the pH adjusted to 6.6-7.0, after which the composition is subjected to high-temperature short-time (HTST) processing during which the composition is heat treated, emulsified and homogenized, and then allowed to cool. Water soluble vitamins and ascorbic acid are added, the pH is adjusted to the desired range if necessary, flavors are added, and water is added to achieve the desired total solid level. The composition is then aseptically packaged to form an aseptically packaged nutritional emulsion. This emulsion can then be further diluted, heat-treated, and packaged to form a ready-to-feed or concentrated liquid, or it can be heat-treated and subsequently processed and packaged as a reconstitutable powder, e.g., spray dried, drymixed, agglomerated.

In summary, methods for preventing or mitigating an acute allergic response in a subject are disclosed. The methods make use of benign compounds, thereby providing a method for mitigating or preventing allergies in patient populations for whom pharmaceutical treatments are inappropriate. The methods make use of compounds that provide a means for targeting the actions of mast cells, a local and systemic regulator of acute allergic responses, thereby expanding the types of acute allergic responses that can be mitigated or prevented. The methods make use of compounds that are also able to regulate the level of nervous system messenger proteins, thereby providing a means to mitigate or prevent acute allergic reactions involving more than just the actions of the immune system. The methods also make use of compounds that promote the growth of immune-stabilizing microbes, thereby complementing and counteracting the negative impact of other acute allergic response mitigation and prevention options.

EXAMPLES

The following examples illustrate specific and exemplary embodiments, features, or both, of the methods disclosed herein. While the examples make use of two specific HMOs described herein, it should be recognized that the protocols described hereinafter can be used to test the ability of any HMO, and nutritional compositions made therefrom, to mitigate or prevent acute allergic responses. The examples are provided solely for the purpose of illustration and should not be construed as limitations on the present disclosure.

Example 1

HMOs Attenuate Mast Cell Degranulation, an Indicator of the Local or Systemic Mast Cell Response A. Cells Exposed to 6'-SL, But Not 2'-FL, Exhibit Attenuated Mast Cell Degranulation in an In Vitro Exposure Assay.

The ability of HMOs to attenuate mast cell degranulation was tested by exposing sensitized bone marrow mast cells (BMMC) to either 2'-FL or 6'-SL.

Figure 1A:
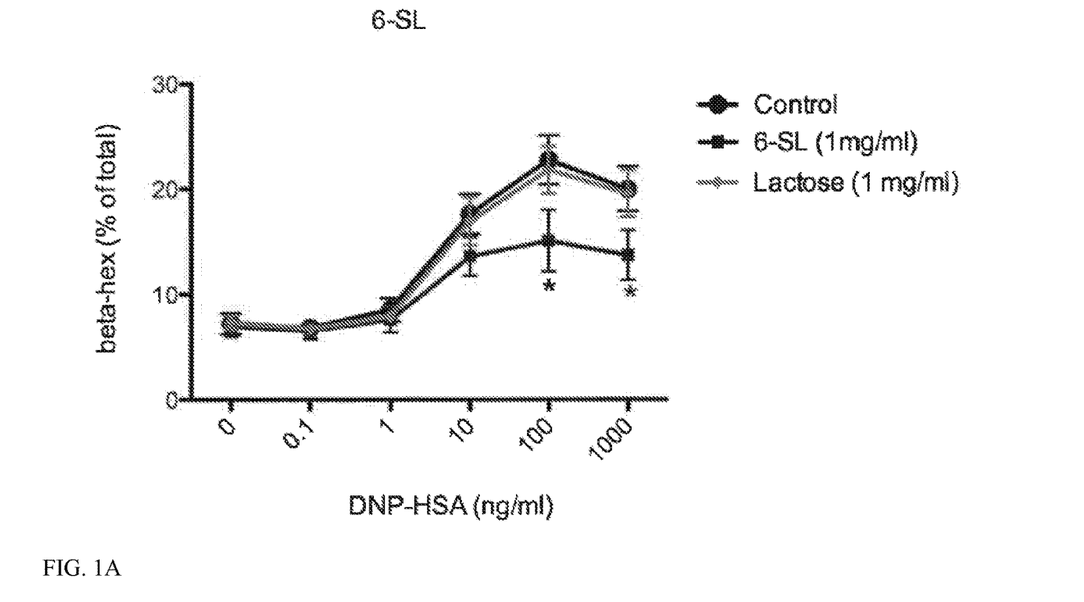
FIG. 1 provides graphs showing the amount of mast cell degranulation in bone marrow mast cells exposed to various HMOs as tested in example 1(A).
Figure 1B:
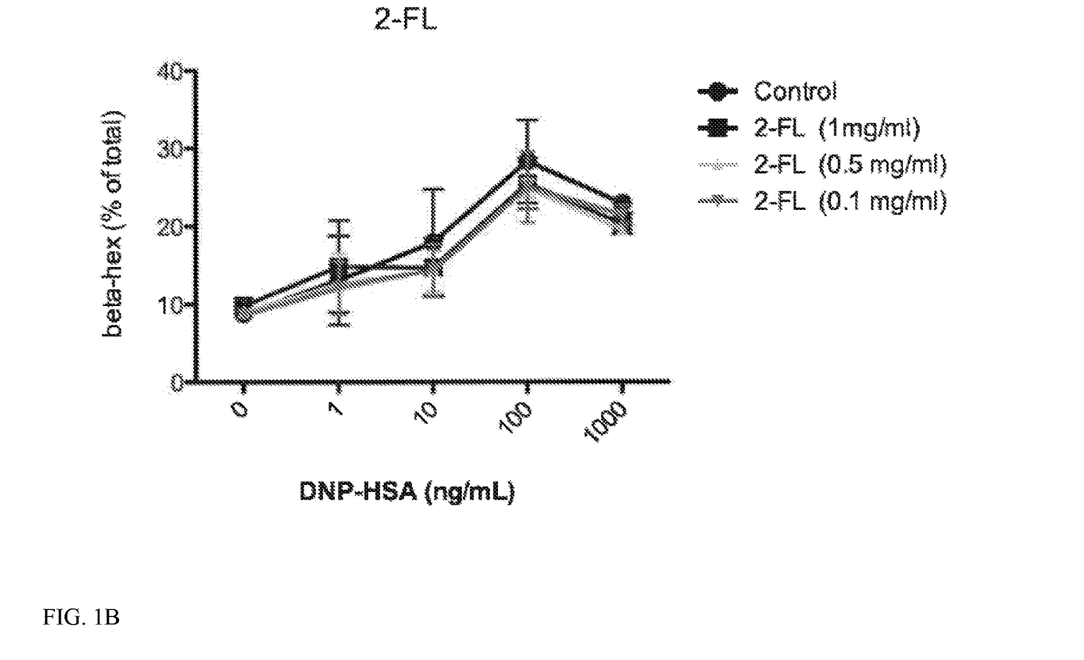

BMMC from female Balb/c mice were obtained by culturing the bone marrow cells in enriched RPMI-1640 medium with 10% pokeweed mitogen-stimulated spleen as a source of mast cell growth factors for 3 weeks. The cells were kept at a concentration of $0.2 \times 10^5$ cells/ml in a 5% $CO_2$, 37° C. environment, where the medium was changed weekly. BMMC were used for experiments after 3-4 weeks of culture (>95% mast cells). BMMC were sensitized with 1ug/ml monoclonal anti-dinitrophenyl (DNP) IgE clone and seeded into 96-well plates at a final concentration of $1 \times 10^6$ cells/ml. Cells were then exposed to HMOs (either 2'-FL or 6'-SL) at a range of concentrations for 30 min prior to activation with DNP-HSA (dinitrophenyl-human serum albumin). Cell supernatants were harvested 30 min after DNP-HSA stimulation and stored at −20° C. until analyzed. An enzymatic colorimetric assay (described in section B, below) was used to detect the release of the granular enzyme hexosaminidase. Results are expressed as a percentage of total β-hexosaminidase. As shown in FIG. 1(A) and (B), 6'-SL (FIG. 1A), but not 2'-FL (FIG. 1B), produced a significant decrease in β-hexosaminidase (β-Hex) activity relative to controls.

B. Mice Fed 2'-FL Exhibit Attenuated Mast Cell Degranulation.

The ability of 2'-FL to attenuate mast cell degranulation was tested in an assay where mice were fed compositions with 2'-FL via oral gavage (200 μl of 5 mg/ml in PBS) for 5 days.

Mice were then euthanized, trunk blood was collected from each mouse, placed in 1.5 ml microcentrifuge tubes and settled for 10 minutes. The samples were spun at 18000 g for 10 minutes at 4° C. on an IEC Centra GP80R centrifuge. Serum was aliquoted in 25 μl aliquots and stored at −80° C. Sensitized BMMC were then exposed to the serum from mice fed 2'-FL at a range of concentrations for 30 min prior to activation with DNP-HSA. Sensitized BMMC preparation and DNP-HSA activation was carried out as described in section A, above.

β-Hexosaminidase Assay

To measure mast cell degranulation, an enzymatic colorimetric assay was used to detect the release of the granular enzyme hexosaminidase, a marker for degranulation activity.

This assay was conducted to assess in-vitro antigen-induced degranulation of mast cells. Mast cells ($1 \times 10^6$ cells/ml), were resuspended in Hepes-Tyrode buffer (HTB) and sensitized for 2 hours at 37° C. with 100 μg/ml of monoclonal IgE antibody against dinitrophenyl haptenic group (anti-DNP) (Sigma, St. Louis, Mo). Subsequently, mast cells were washed with HTB and challenged for 30 minutes with serum isolated from mice which had been fed with HMO (oral gavage 200 μl of 5 mg/ml in PBS) for 5 days. The release of β-hexosaminidase from mast cells was measured from the supernatant. 100 μl of supernatant were mixed with 50 μl of β-hexosaminidase substrate (80 μl of 1 mM 4-methylumbelliferyl-N-acetyl-β-D-glucosaminide diluted in 5 ml of glycine buffer pH 10.7) for 2 hours at 37° C. The reaction was stopped with 100 μl citrate buffer pH 4.5 and read by using CytoFluor 2350 fluorescent spectrophotometer at 450 nm (excitation 356 nm). Β-hexosaminidase release was presented as a percentage of the total Β-hexosaminidase release determined by cell lysis with 1× triton-X.

Figure 2:
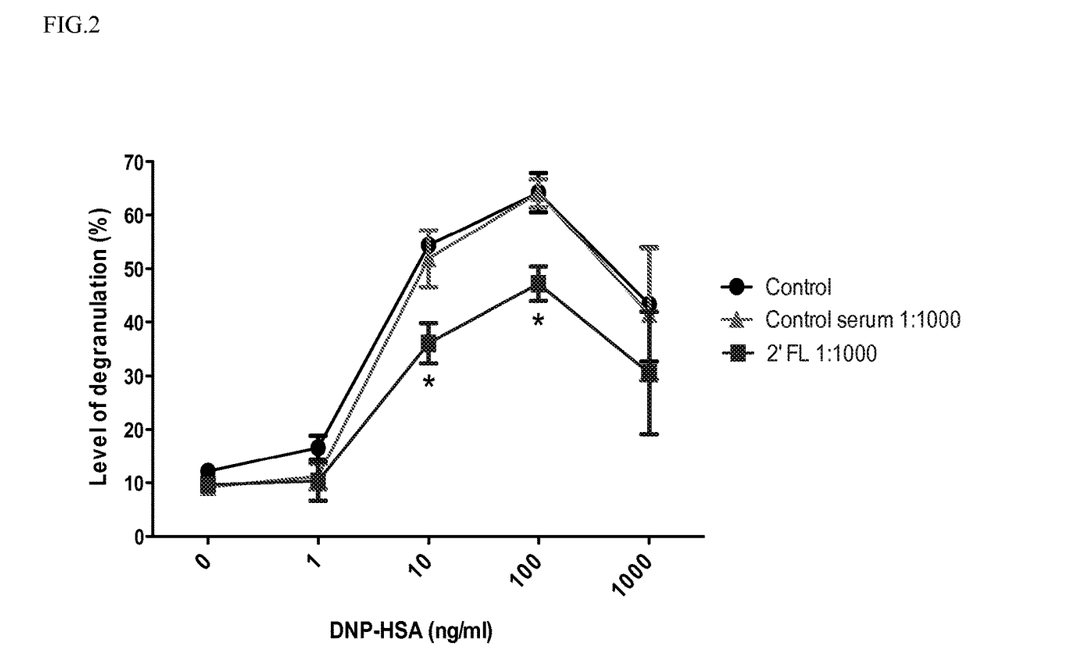
FIG. 2 is a graph showing the amount of mast cell degranulation in mice fed 2'-FL as tested in example 1(B).

As shown in FIG. 2, serum from mice fed 2'-FL demonstrated a significant decrease in mast cell degranulation relative to controls.

Example 2

HMOs Attenuate Passive Cutaneous Anaphylaxis (PCA), an Indicator of the Skin Mast Cell Response The ability of HMOs to attenuate skin mast cell responses, as measured by the PCA response, was determined in sensitized mice fed 2'-FL, phosphate buffered saline (PBS), lactose, or 6'-SL by detecting the level of dye in ear pinnae indicative of the PCA response.

Figure 3:
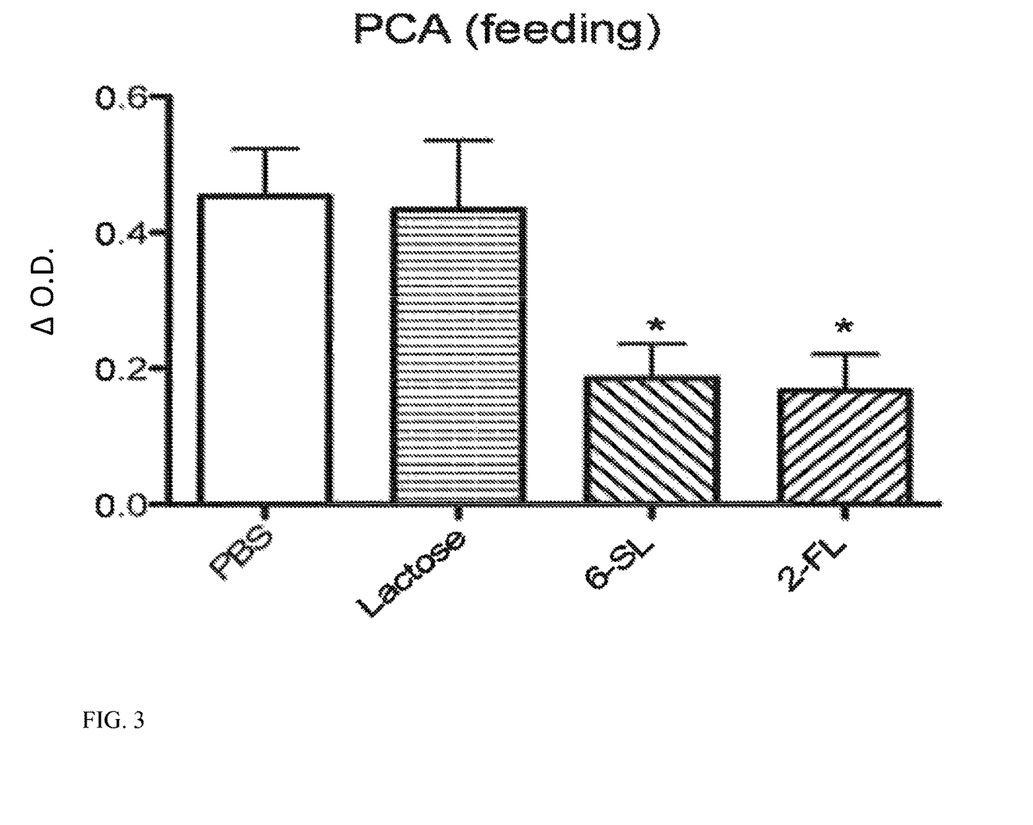
FIG. 3 is a graph showing the skin mast cell response in mice treated with various HMOs as tested in example 2.

Mice were treated with 2'-FL, 6'-SL, lactose or PBS by oral gavage (1 mg per mouse) daily for 5 days. On day 4 mice were sensitized by intradermal (i.d.) injection of anti-DNP IgE (10 ng in 10 m L saline) into the right ear pinnae while the left ear was injected with saline alone. Twenty-four hours later, DNP-HSA (10 mg/kg) together with Evans blue (100 mg/kg) was injected intravenously (i.v.). 1 hour following i.v. injection mice were euthanized and ear pinnae collected. Evans blue dye was extracted by incubating the skin samples in DMSO for 24 h at 37° C., and measuring the optical density (O.D.) at 650 nm. Data is presented as the difference in O.D. between the control (left) and sensitized (right) ear. As shown in FIG. 3, there was a greater difference in dye detected between right and left ears in PBS and lactose-treated mice than in mice treated with 2'-FL or 6'-SL.

Example 3

2'-FL, but Not 6'-SL, Attenuates the Gastrointestinal Mast Cell Response

The ability of HMOs to attenuate the gastrointestinal mast cell response was determined by measuring the amount of diarrhea, change in body temperature, and change in mouse mast cell protease-1 (mMCP-1) levels in HMO treated mice relative to untreated and lactose treated control mice.

The OVA-induced food allergy model was modified from Yamaki and Yoshino (Allergy. 2012; 67:1259-70). Mice were sensitized with 50 μg of OVA (Sigma, St. Louis, Mo.) and 2 mg of alum (Sigma, St. Louis, Mo.) in 200 μl of Phosphate Saline Buffer (PBS) on day 0 and 14. HMO (200 ul of 5 mg/ml in PBS) treatments (2'-FL or 6'-SL) were administrated daily via oral gavage from day 27 to day 49. Mice were orally challenged with 50 μg of OVA every 3 days (Days: 28, 31, 34, 37, 40, 43, 46 and 49). On challenge days treatments were given 1 hour prior to OVA challenge. On day 49, serum, spleen and intestinal samples, were obtained. Non-sensitized PBS challenged mice served as negative controls.

A. Treatment with 2'-FL, But Not 6'-SL, Significantly Decreases Diarrhea Symptoms.

Figure 4A:
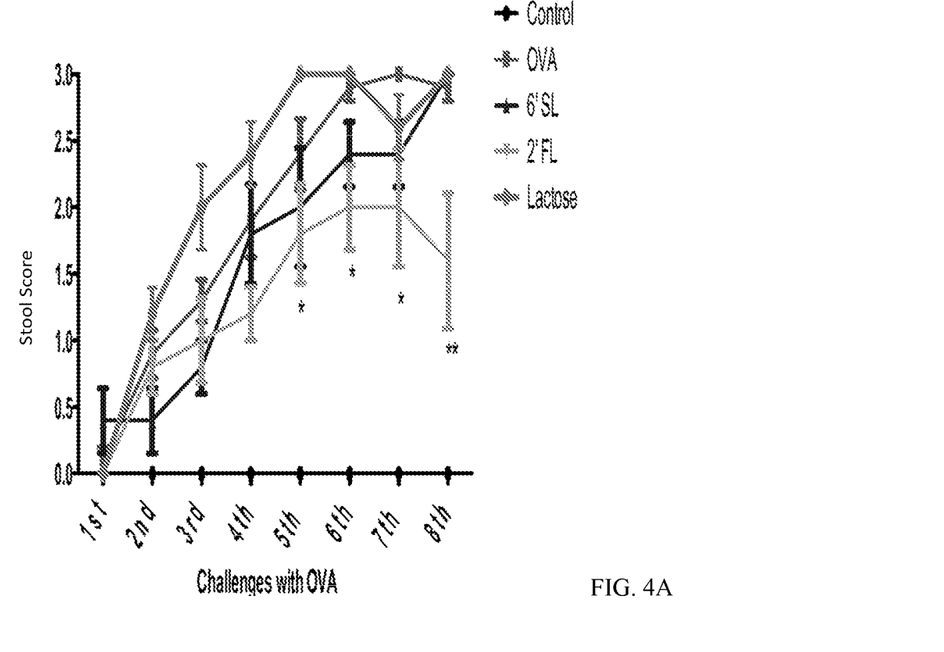
FIG. 4 provides graphs showing the extent of diarrhea produced by mice exposed to various treatments as tested in example 3(A).
Figure 4B:
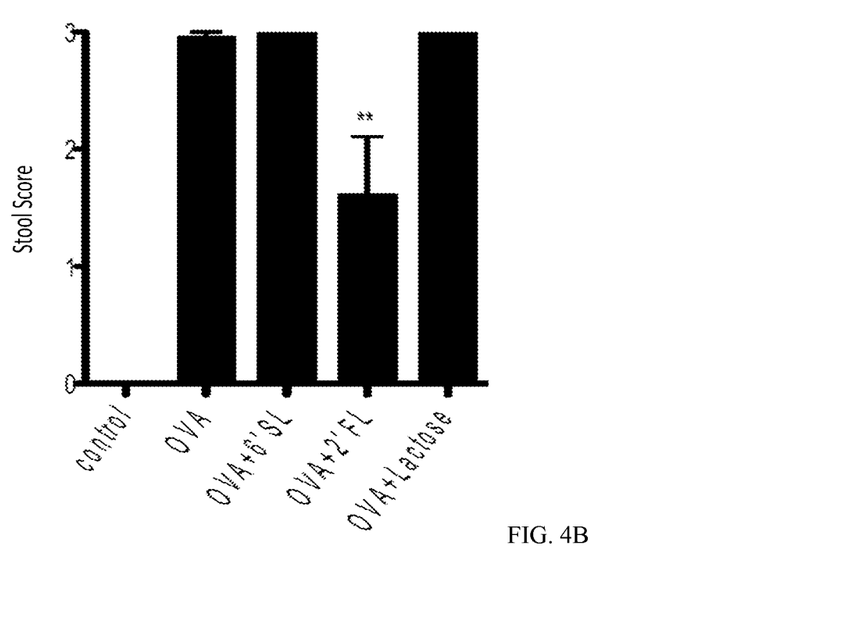

Diarrhea symptoms were scored by visually monitoring mice for 60 minutes after challenge as follows: 0, normal stools; 1, a few wet an unformed stools; 2, a number of wet an unformed stools with moderate perianal staining of the coat; 3, severe, watery stool with severe perianal staining of the coat. As shown in the line and bar graphs of FIG. 4(A) and FIG. 4(B), respectively, 2'-FL treated, OVA-sensitized mice had a significantly lower stool score than untreated or lactose treated, OVA-sensitized mice.

B. Treatment with 2'-FL, But Not 6'-SL, Mitigates the Decline in Rectal Temperature Caused by OVA Sensitization.

Figure 5A:
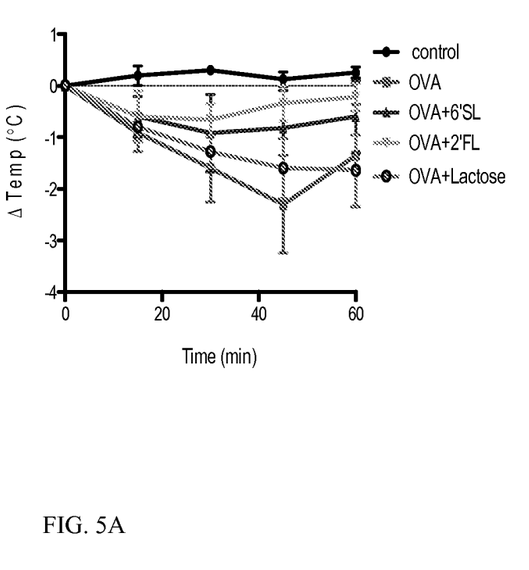
FIG. 5 provides graphs showing the change in rectal body temperature of mice exposed to various treatments as tested in example 3(B).
Figure 5B:
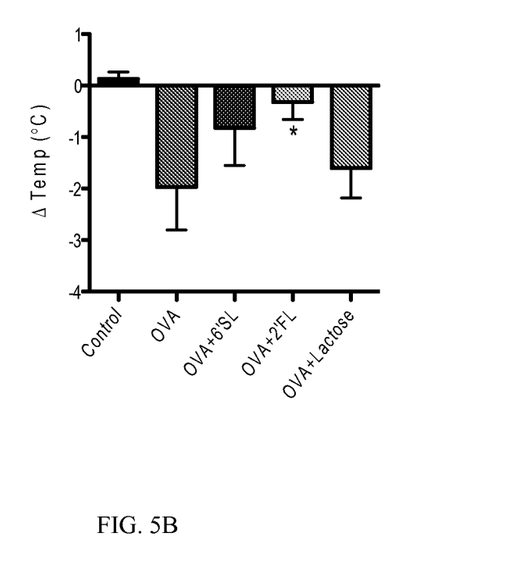

Rectal temperature was monitored for 1 hour following the final antigen challenge. As shown in the line and bar graphs of FIG. 5(A) and FIG. 5(B), respectively, 2'-FL treatment of OVA-sensitized mice mitigated the decline in rectal temperature seen in untreated or lactose treated, OVA-sensitized mice.

C. Treatment with 2'-FL, But Not 6'-SL, Significantly Decreased the serum mMCP-1 Levels Caused by OVA Sensitization.

Figure 6:
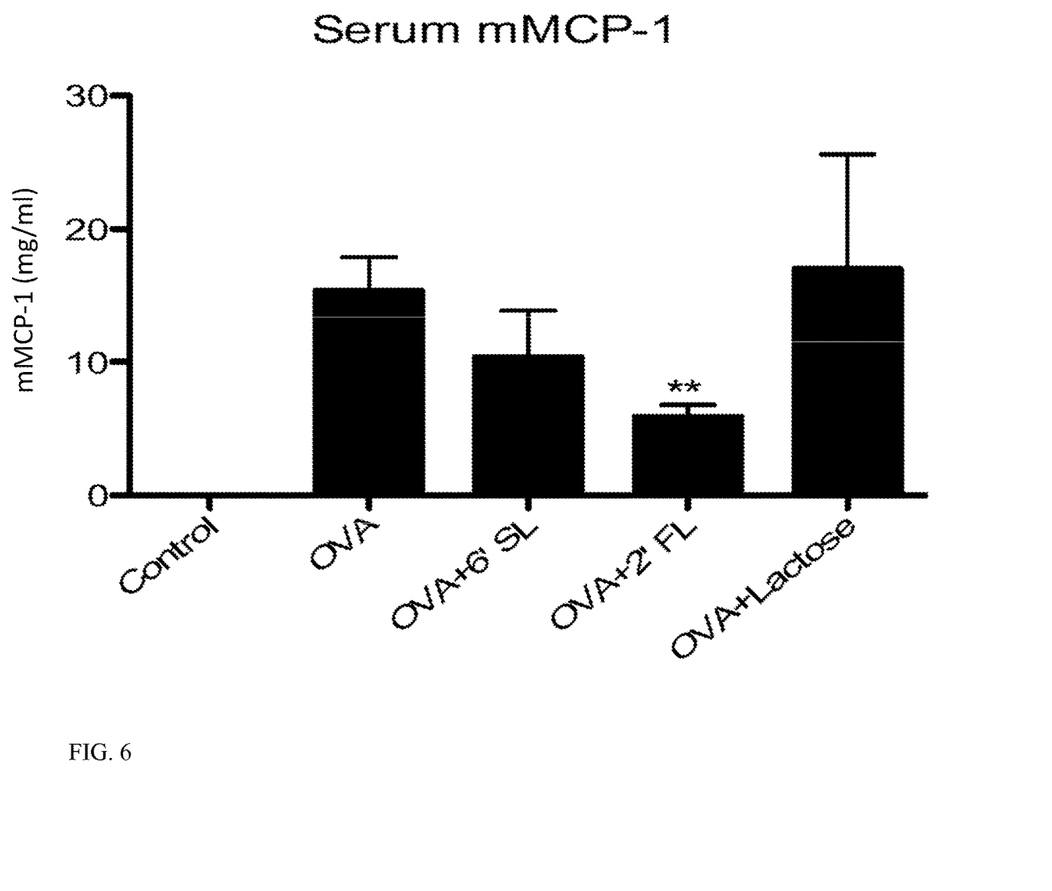
FIG. 6 is a graph showing the level of mouse mast cell protease-1 in mice exposed to various treatments as tested in example 3(C).

Following body temperature measurements, mice were euthanized and serum mMCP-1 concentration was determined. As shown in FIG. 6, treatment with 2'-FL, but not 6'-SL, produced a significant decrease in mMCP-1 levels relative to untreated and lactose treated, OVA-sensitized controls.

We claim:

1. A method for mitigating an acute allergic response in a subject in need thereof, the method comprising administering a nutritional composition to the subject, wherein the nutritional composition comprises at least one human milk oligosaccharide (HMO) selected from the group consisting of 2'-fucosyllactose (2'-FL), 6'-sialyllactose (6'-SL), and combinations thereof, wherein the nutritional composition does not contain an N-acetyl-lactosamine; and wherein the nutritional composition comprises lactose in an amount of 0% to 55% relative to total carbohydrate in the nutritional composition.

2. The method of claim 1, wherein the acute allergic response comprises one or more mast cell mediated immediate allergic response.

3. The method of claim 2, wherein the one or more mast cell mediated immediate allergic response is selected from the group consisting of a skin mast cell response, a gastrointestinal mast cell response, and a respiratory mast cell response.

4. The method of claim 2, wherein the nutritional composition comprises either 2'-FL or 6'-SL, but not both.

5. The method of claim 2, wherein a nutritional composition comprising either 2'-FL or 6'-SL, or both, is administered to the subject to mitigate an acute allergic response comprising more than one mast cell mediated immediate allergic response.

6. The method of claim 4, wherein a nutritional composition comprising 2'-FL is administered to the subject to mitigate one mast cell mediated immediate allergic response.

7. The method of claim 4, wherein a nutritional composition comprising either 2'-FL or 6'-SL is administered to the subject to mitigate a skin mast cell response.

8. The method of claim 4, wherein a nutritional composition comprising 2'-FL is administered to the subject to mitigate a gastrointestinal mast cell response.

9. The method of claim 5, wherein a nutritional composition comprising both 2'-FL and 6'-SL is administered to the subject to mitigate an acute allergic response comprising more than one mast cell mediated immediate allergic response.

10. The method of claim 1, wherein the nutritional composition further comprises at least one of a protein source, a carbohydrate source, and a fat source.

11. The method of claim 1, wherein the nutritional composition is administered orally.

12. The method of claim 1, wherein the nutritional composition is administered topically.

13. The method of claim 1, further comprising administering an antihistamine to the subject.

14. The method of claim 13, wherein the antihistamine comprises a compound selected from the group consisting of loratadine, fexofenadine, and cetirizine.

15. The method of claim 1, further comprising administering an eicosanoid inhibitor to the subject.

16. The method of claim 15, wherein the eicosanoid inhibitor comprises a compound selected from the group consisting of inhibitors of thromboxanes, prostaglandins, and leukotrienes.

17. The method of claim 1, wherein the nutritional composition further comprises a carbohydrate selected from the group consisting of maltodextrin, corn syrup solids, and sucrose.

18. The method of claim 1, wherein the nutritional composition further comprises a hypoallergenic form of galacto-oligosaccharide.

\* \* \* \* \*